United States Patent
Rosiello

(10) Patent No.: US 7,645,377 B2
(45) Date of Patent: *Jan. 12, 2010

(54) BLOOD PRODUCT TRANSFER SYSTEM

(75) Inventor: Keith Rosiello, Shrewsbury, MA (US)

(73) Assignee: ZymeQuest, Inc., Beverly, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 11/326,628

(22) Filed: Jan. 6, 2006

(65) Prior Publication Data

US 2006/0113228 A1    Jun. 1, 2006

Related U.S. Application Data

(63) Continuation of application No. 10/232,197, filed on Aug. 28, 2002, now Pat. No. 7,011,742.

(60) Provisional application No. 60/322,387, filed on Sep. 14, 2001.

(51) Int. Cl.
*A61M 1/02* (2006.01)
*C02F 1/38* (2006.01)

(52) U.S. Cl. .............. 210/109; 210/258; 604/410; 494/85; 383/9; 383/37; 383/906; 141/114

(58) Field of Classification Search .......... 210/109, 210/257.1, 416.1, 258; 604/410, 140, 409, 604/6.11, 408, 411, 326; 383/906, 9, 37; 494/85, 45; 137/505.16; 141/114, 166, 10, 141/11, 237; 128/DIG. 24; 222/207
See application file for complete search history.

(56) References Cited

U.S. PATENT DOCUMENTS

| 4,433,974 A | | 2/1984 | Bischof |
| 4,564,359 A | | 1/1986 | Ruhland |
| 5,141,490 A | | 8/1992 | Fujii et al. |
| 5,269,924 A | * | 12/1993 | Rochat ............... 210/445 |
| 5,632,906 A | | 5/1997 | Ishida et al. |
| 5,665,048 A | | 9/1997 | Jorgensen |
| 5,690,815 A | * | 11/1997 | Krasnoff et al. ........ 210/97 |
| 5,695,653 A | * | 12/1997 | Gsell et al. ........... 210/767 |
| 6,175,420 B1 | | 1/2001 | Barry et al. |
| 6,325,750 B1 | | 12/2001 | Jorgensen et al. |

FOREIGN PATENT DOCUMENTS

| EP | 0 405 094 | | 1/1991 |
| JP | 05237183 A | * | 9/1993 |

OTHER PUBLICATIONS

International Search Report; Date of Mailing Dec. 6, 2002.

* cited by examiner

*Primary Examiner*—Terry K Cecil
(74) *Attorney, Agent, or Firm*—Foley & Lardner LLP; Michel Morency; James F. Ewing

(57) ABSTRACT

A system for transferring blood product between a blood storage bag and a processing bag. The system includes an airtight containment chamber for supporting therein one or more blood storage bags. A door is provided for access to the chamber and there is included an airtight fixture that allows tubing from the blood storage bag to exit the chamber. A fluid pump is coupled to the containment chamber for establishing either pressure or vacuum within the containment chamber. A controller controls the air pump to, in turn, control the transfer of a blood product.

12 Claims, 7 Drawing Sheets

BLOOD PRODUCT TRANSFER SYSTEM

This application is a Continuation of U.S. patent application Ser. No. 10/232,197, filed Aug. 28, 2002, now U.S. Pat. No. 7,011,742, which claims benefit under 35 U.S.C. § 119(e) of U.S. Provisional Application No. 60/322,387, filed on Sep. 14, 2001, the entire contents of which are incorporated herein by reference.

BACKGROUND OF THE INVENTION

1. Field of the Invention

The present invention relates in general to a fluid product transfer system, and pertains, more particularly, to a system for transferring blood product between a blood storage bag and a processing bag, or vice versa. The principles of the present invention may be applied in a centrifuge processing system or other extracorporeal blood processing systems.

2. The Prior Art

In current blood processing systems there are generally two techniques for moving blood product from a flexible blood storage bag to a processing device such as a centrifuge. These two techniques include gravity and peristaltic pumps currently used to create blood flow in the coupling tubing.

Regarding the gravity technique, the blood storage bag is typically disposed at a position higher than the processing bag and blood flows from the bag to the lower disposed centrifuge by gravitational force. The gravitational technique is adequate if the bag is high enough, the tubing diameter large enough, and the tubing length is short enough to expedite fluid flow. For some applications in which the tubing inside diameter is narrow, the length of tubing is relatively long. Thus, the required height to provide a reasonable drain time would make the gravity technique impractical. The deficiency of the gravity technique is that the tubing size has to be of sufficient inside diameter to allow adequate flow or otherwise the fluid may clot, particularly if platelets are part of the fluid, and thus impede flow. In addition, if the inside diameter of the tubing is not sufficient this may cause the blood product to flow very slowly because of the relatively high viscosity of the blood related components. Another drawback to the gravity technique is that it only allows blood to flow in one direction, essentially from the blood storage bag to the processing device, unless positions are reversed.

The second technique for moving blood products to a processing device such as a centrifuge is with the use of a pump such as a peristaltic pump. These pumps are functional in terms of flow but their drawback is that they can cause damage to the blood product, particularly red blood cells. The roller wheels on peri-pumps tends to put a significant amount of pressure in a very small area of a tube where the blood is flowing, thereby destroying some of the red blood cells that come into contact with the roller wheels.

SUMMARY OF THE INVENTION

Accordingly, it is an object of the present invention to provide an improved blood product transfer system that enables the blood product to readily flow through smaller diameter tubes with great efficiency and speed.

Another object of the present invention is to provide a blood product transfer system that operates so as to keep the red blood cells or any other components of the blood product free from any damaging effects and in a sterile, closed environment.

To accomplish the foregoing and other objects, features and advantages of the invention there is provided a system for transferring blood product between a blood storage bag and a processing bag, usually a centrifuge processing bag. The system is comprised of an airtight containment chamber that is provided with means supported within the chamber, preferably at the top thereof, for supporting at least one blood storage bag, and usually a plurality of such bags. In a preferred orientation, the blood storage bag is supported in an upright position with a tubing end of the blood storage bag at the bottom thereof. The airtight containment chamber is provided with a door including an airtight fixture that allows tubing from the blood storage bag to exit the chamber, such as for coupling by way of a distribution module to a processing module. A fluid pump is coupled to the airtight containment chamber for establishing either pressure within the chamber or drawing a vacuum in the chamber so as to transfer blood product, in one instance under pressure from the blood storage bag to the processing bag, and in the other instance, using vacuum for transferring fluid from the processing bag back to a blood storage bag. A controller is used for controlling at least the fluid pump to, in turn, control this transfer of blood product.

As indicated previously, the airtight containment chamber may be for supporting a plurality of storage bags. These bags are disposed in a position that allows the blood product to flow due to pressure or vacuum without allowing a blockage to occur via a collapsed tube or blood storage bag. The fluid pump may comprise an air pump having a compressor for delivering either a pressure to the chamber or drawing a vacuum on the chamber. A control solenoid circuit may be provided for selecting, in one state, pressure operation, and in another state, vacuum operation. These one and another states are mutually exclusive.

In accordance with other aspects of the present invention the airtight containment chamber may include a fluid control circuit that couples either pressure or vacuum to the chamber. In this embodiment some of the bags in the chamber are subjected to pressure during a first time interval and others of the bags are subjected to vacuum during a second time interval.

In accordance with another embodiment of the present invention there may be a pair of airtight containment chambers, one for coupling to a vacuum source and the other for coupling to a pressure source. This may comprise an air control circuit coupled between the pump and the chambers for directing only pressure to one chamber and only vacuum to the other chamber. Each of chambers may include a door. The chambers may be separated by a common dividing wall.

In accordance with still another embodiment of the present invention there may be provided a pair of pumps and an associated pair of chambers with a pump associated with each respective chamber. In this embodiment only vacuum is coupled to one chamber and only pressure is coupled to the other chamber. The chambers may be separated and each have its own access door.

BRIEF DESCRIPTIONS OF THE DRAWINGS

Numerous other objects, features and advantages of the invention should now become apparent upon a reading of the following detailed description when taken in conjunction with the accompanying drawings, in which.

DETAILED DESCRIPTION OF THE INVENTION

The drawings, that are to be discussed hereinafter, illustrate a chamber for storing blood product bags or any other fluid bags in which the fluid is to be driven or transferred without requiring the use of peri-pumps or gravity. In accordance with one embodiment of the invention only pressure may be applied within the containment chamber for the purpose of expressing the blood product to, for example, a centrifuge, such as to a centrifuge processing bag. In another embodiment in accordance with the invention the chamber may be operated under vacuum so as to transfer blood products say from a blood processing bag to a blood product storage bag within the chamber.

Thus, the present invention describes, in essence, a mechanical device that is a pressure and/or vacuum chamber that facilitates the flow of blood or blood related product fluids to and/or from a centrifuge for blood related processing. The blood product may be contained in medical industry standard blood or transfer bags with attached sealed tubing. The blood related product may include platelets, plasma, red blood cells, in any combination or separately, and in any quantity up to the capacity of the bags in which they are contained. For the purpose of this invention, the term "blood product" may include, but is not necessarily limited to, treated or untreated fluid associated with blood, warm or cold blood, stored or fresh blood, blood diluted with a physiological solution, including but not limited to saline, nutrient, and/or anticoagulant solutions, one or more blood components, such as platelet concentrate, platelet rich plasma, fresh frozen plasma, plasma, plasma derivatives such as cryoprecipitate, packed red blood cells, or buffy coat, and analogous products derived from blood or blood components.

One objective of the present invention is to generate flow of blood product fluids say from one sterile flexible blood bag or multiple sterile flexible blood bags, to a centrifuge sterile processing bag or multiple centrifuge sterile processing bags. For this aspect of the invention air pressure is used within a chamber containing the blood product bags. A second objective is to generate flow of blood product fluids from a centrifuge sterile processing bag or multiple centrifuge sterile processing bags, to one sterile flexible blood bag or multiple sterile flexible blood bags. To accomplish this a vacuum is used within the chamber containing the blood product bags.

Figure 1:
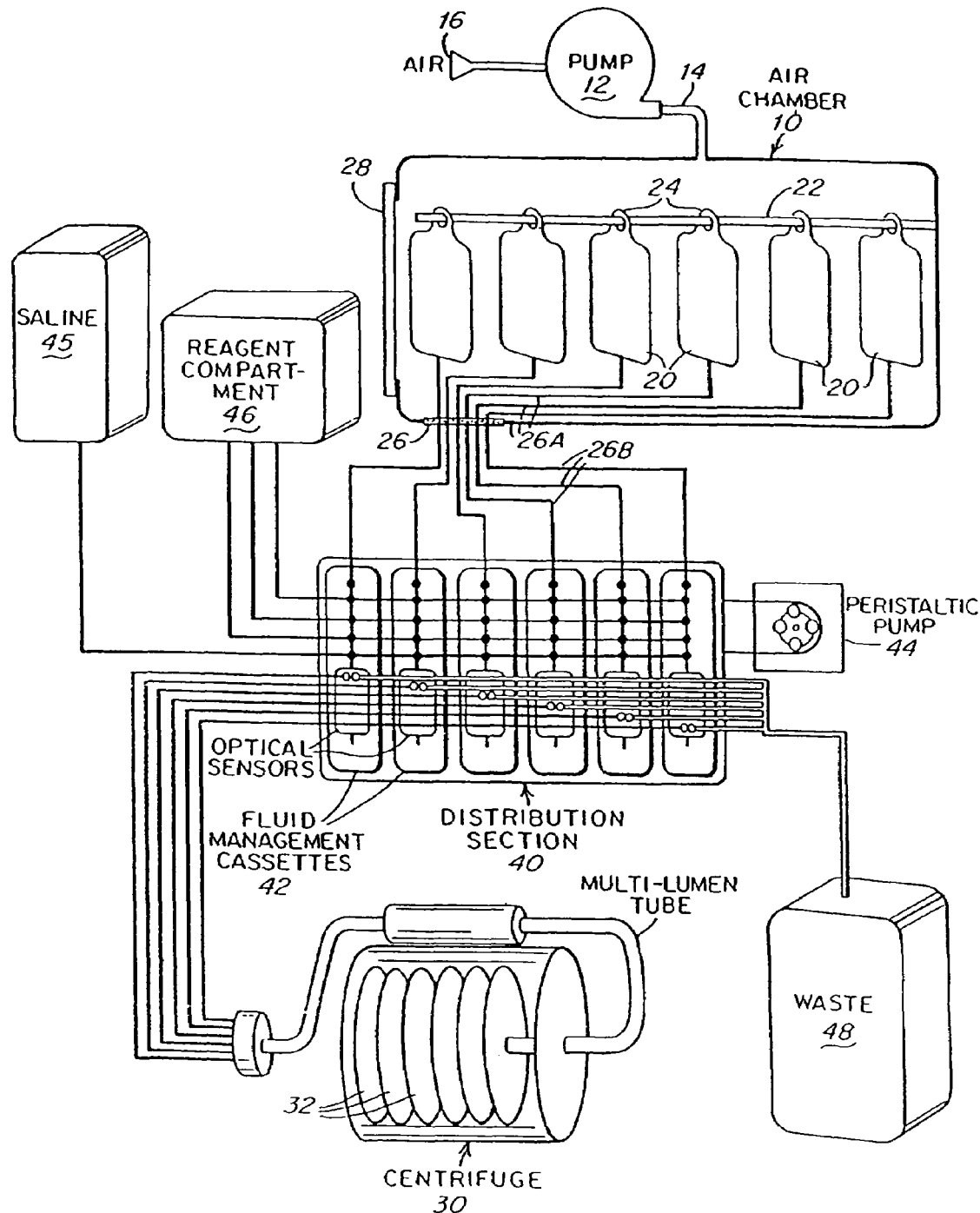
FIG. 1 is a system block diagram illustrating a system in which the blood product transfer apparatus of the present invention may be employed.

Reference is now made to FIG. 1 which is a system block diagram of a cell processing system embodying the device for enabling transfer of blood product between at least one blood storage bag and a centrifuge processing bag. Many of the components illustrated in FIG. 1 are not described in detail herein. However, reference is made to U.S. Pat. No. 6,175,420 to Barry et al., granted Jan. 16, 2001 for a more comprehensive description of fluid management portions of the system. Reference may also be made to U.S. Pat. No. 5,665,048 to Jorgensen, granted Sep. 9, 1997 for further descriptions relating to the centrifuge itself. Both U.S. Pat. Nos. 5,665,048 and 6,175,420 are incorporated herein by reference, in their entirety.

FIG. 1 illustrates the vacuum/pressure chamber 10 in accordance with the present invention and the associated pump 12 that couples to the airtight containment chamber 10 by way of the tubing 14. FIG. 1 also illustrates the air supply at 16. Schematically illustrated within the chamber 10 are a series of blood product storage bags 20. Each of these bags is supported from a hanger 22 by means of a securing loop 24 associated with each bag. Individual lines or tubing from each bag couples through the wall of the chamber by way an airtight fixture 26. FIG. 1 illustrates this fixture at the bottom of the chamber 10. However, in embodiments to be described in further detail hereinafter, the fixture is usually provided on the door end and at about a mid-level position in the door, such as in, for example, FIG. 2. FIG. 1 also illustrates the door 28 to the chamber 10.

In FIG. 1 there is also illustrated a centrifuge 30 that may have associated therewith centrifuge processing bags 32. Also illustrated is the distribution section 40 comprising a plurality of fluid management cassettes 42 and a peristaltic pump 44. Also coupling to the cassettes 42 is a saline supply or bag 45 and reagent compartment 46. Also illustrated is a waste bag 48 relating to the fluid management cassettes.

Not specifically illustrated in FIG. 1, but considered as part of the system, is a computer controller. This is illustrated, however, in other embodiments of the present invention described hereinafter. This is described as a processor control 50 that controls, inter alia, operation of the air pump in accordance with the present invention.

Figure 2:
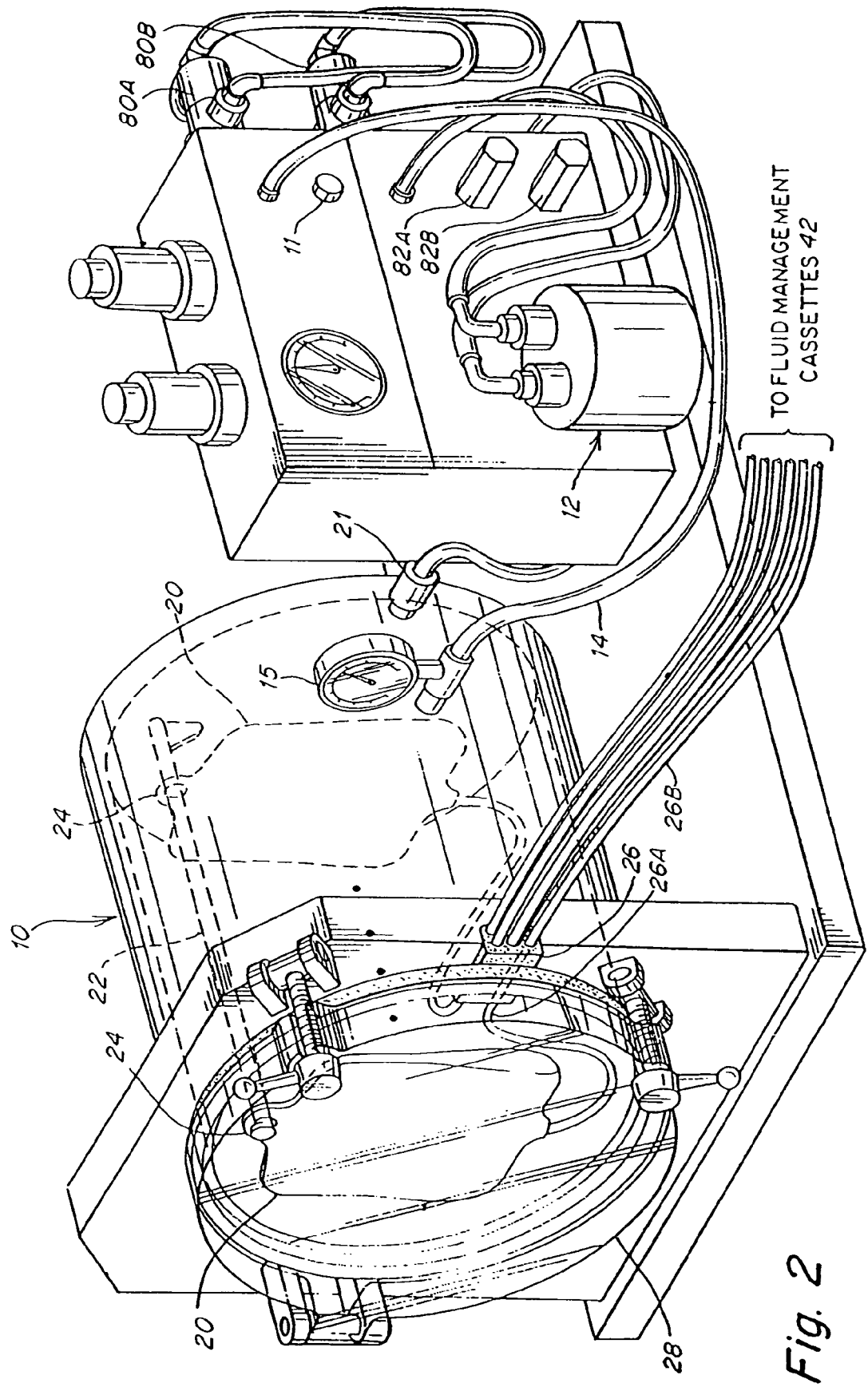
FIG. 2 is a perspective view of the air chamber of the present invention.
Figure 4:
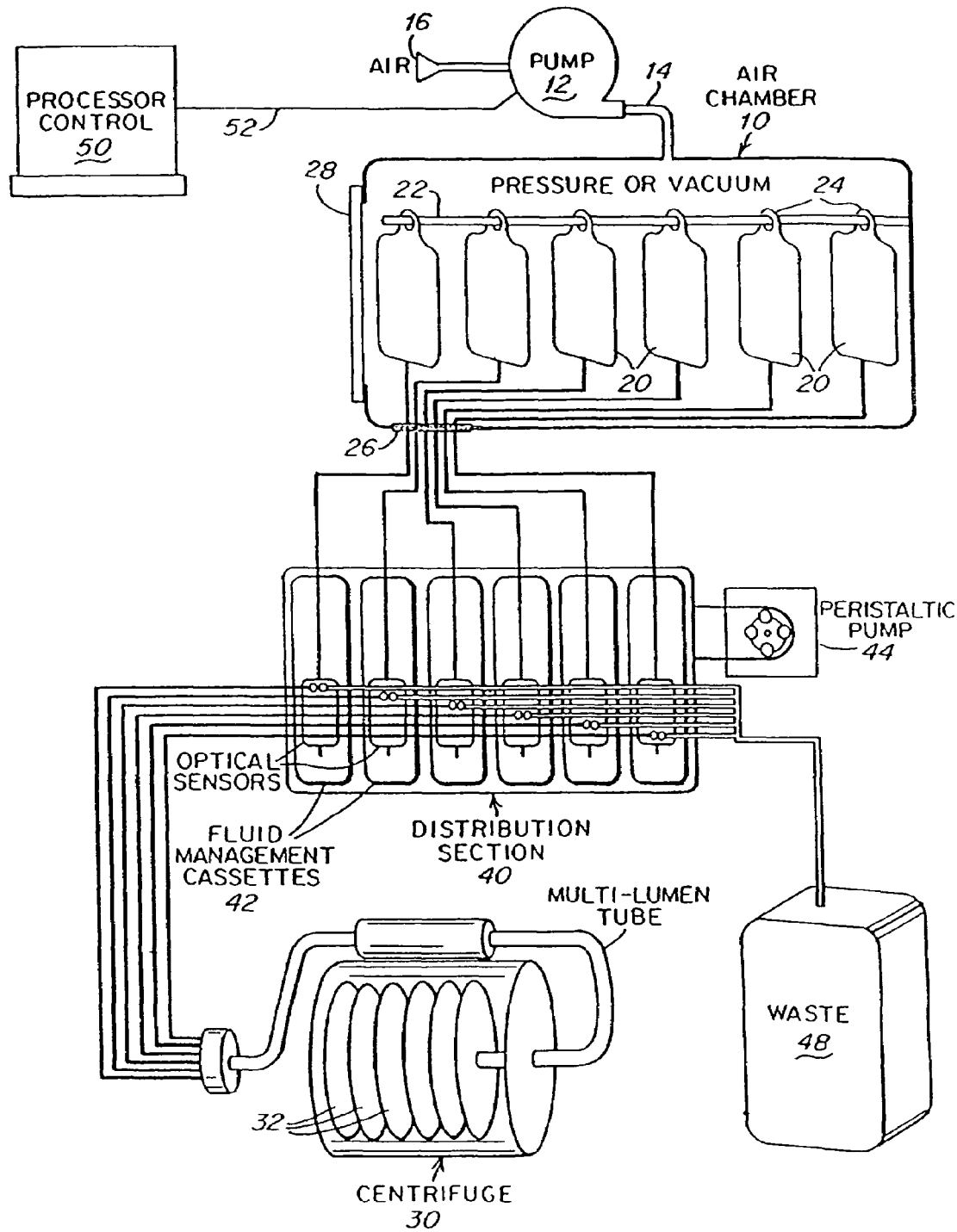
FIG. 4 is a system block diagram illustrating an embodiment of the invention employing a single pump with multiple blood product storage bags.

Reference may now be made to FIG. 2 of the application for further details of the pressure/vacuum chamber of the present invention. As indicated previously, the concepts of the present invention can be practiced even with the use of only a single bag within the storage chamber. However, a number of bags may be placed in the device chamber, the quantity of which depends on the processing capabilities of the centrifuge, such as whether it is a single or N unit device. The chamber 10 contains an airtight door 28 that allows access and placement of the bags inside the chamber for processing. The airtight door 28 also has an adjoining airtight fixture 26 for allowing the tubing from the blood bags to exit the chamber, so that those tube endings can be sterilely docked to the centrifuge processing tubing. This is illustrated in FIGS. 2 and 4 by various lengths of tubing 26A within the chamber and tubing 26B outside the chamber. The airtight tubing fixture 26 allows for the maximum number of tubes related to the bag capacity of the chamber. Because the blood bags and tubing are not separated or cut, there is no concern for the device to provide a sterile environment. Inside the chamber are one or more hangers, schematically illustrated in FIG. 1 by the hanger 22 for mounting a single bag or a plurality of bags. These bags 20 are preferably mounted vertically so that under pressure, the tubing does not collapse or pinch until the blood product has been removed to the centrifuge, in the pressure application.

The device of the present invention, including the chamber 10 has the capability to provide a gradient level of pressure or vacuum, essentially from no pressure or vacuum to positive pressure or vacuum and over any time interval. The device chamber 10 preferably has a release valve 21 such as depicted in FIG. 2 that may be controlled by the user or by the centrifuge process to release pressure or vacuum to atmospheric conditions. Also, the airtight door 28 to the chamber preferably has a safety mechanism such as safety latch to ensure that the door cannot be opened unless the chamber contains no pressure or vacuum.

The chamber 10 of the device in accordance with the present invention may also have a pressure release valve that may be mounted in the wall of the chamber. This pressure release valve ensures that a pressure or vacuum does not exceed the device chamber limit. The device of the present invention, such as illustrated in FIG. 2 can be constructed as a stand-alone unit with manual control by an operator, or it can be driven automatically by a system that drives an entire process.

The airtight containment chamber is constructed of a material that can withstand large pressures and vacuums. The volumetric capacity of the chamber is great enough to contain one or more flexible blood bags (or blood transfer bags) hung vertically by the bag hanger that runs across the top of the chamber. The door of the chamber is preferably in the form of a clear window, made of lexan or some other strong clear material to allow visibility into the chamber. As indicated previously the door to the chamber is airtight and provides access to place the flexible blood bags inside the chamber. The door has a fixture such as fixture 26 that allows the tubing from the flexible or transfer bags to exit the chamber to the outside of the chamber where the tubing can be attached with a sterilized dock to the processing bags of the centrifuge.

As also illustrated in the drawings, the chamber 10 has associated therewith an air hose 14 that is connected to the exterior pump 12. The pump 12 provides either air pressure or vacuum to the chamber. The chamber has a pressure/vacuum transducer that allows pressure and vacuum readings to be taken and to be preferably processed by the computer processor. Associated with the pump is a switch mechanism that allows it to pump air to the chamber to create pressure, or, alternatively, withdraw air to create a vacuum.

The chamber interlock, the chamber release valve, chamber transducer, air pump and other solenoids needed to control air flow, are all controlled by a computer processor that is itself part of a larger computer system that controls the entire process. This centrifuge system has a user interface that facilitates the process of loading and unloading the pressure and/or vacuum chamber.

Now, and with further reference to the drawings, FIG. 2 illustrates the door 28 to the chamber 10. Also illustrated in FIG. 2 is the hanger 22, showing at least one blood product storage bag 20 supported from the hanger 22. The amount of tubing illustrated in FIG. 2 indicates that there may be up to three bags in the chamber with associated tubing from all three bags. Also illustrated is the tubing fixture 26 that enables tubing 26A associated with the bag, to be coupled to the outside of the chamber to tubing 26B. Tubings 26A and 26B may be the same uninterrupted tubing.

Also, with reference to FIG. 2, there is shown there the chamber 10 and the tubing 14 that couples from the chamber 10 to the air pump 12. Also illustrated in FIG. 2 are the solenoids 80A and 80B that are controlled, to be described in further detail hereinafter, for selecting either vacuum or pressure operation. Also illustrated in FIG. 2 are the vacuum and pressure control valves 82A and 82B.

In FIG. 2, the chamber release valve 21 is also illustrated. Also illustrated is a gauge 15 for reading the pressure or vacuum that occurs in the chamber.

Figure 3:
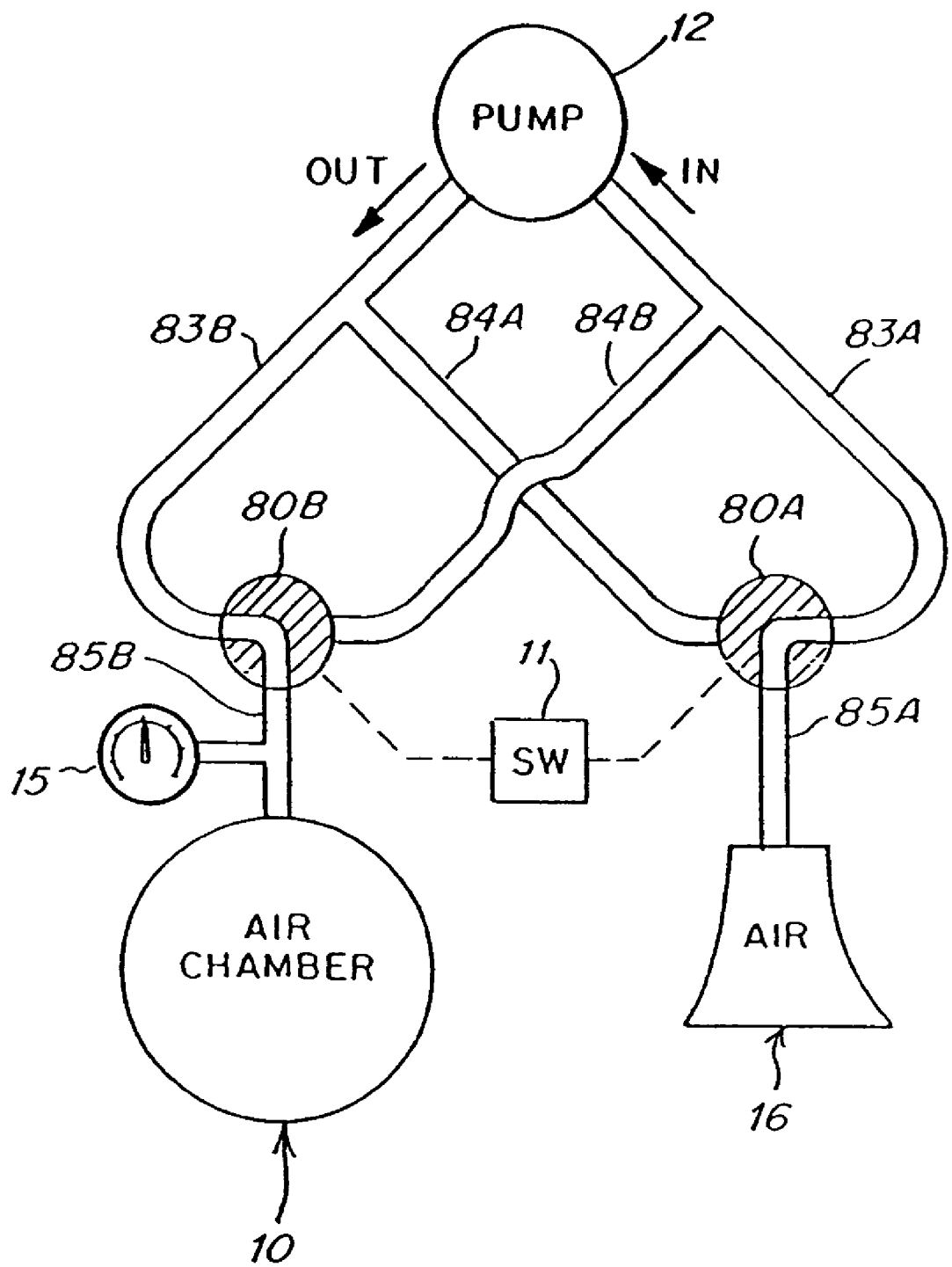
FIG. 3 is a schematic diagram illustrating the fluid pump, chamber and air supply indicating alternate operation for respective pressure and vacuum.

FIG. 3 is a schematic diagram illustrating the pump 12, chamber 10 and air supply 16, along with the solenoids 80A and 80B. Associated with the solenoid 80A are coupling tubing lines 83A, 84A and 85A. Associated with the solenoid 80B are coupling tubing lines 83B, 84B and 85B.

For pressure operation the solenoid 80A is operated so that there is a path between tubing lines 83A and 85A. Similarly, the solenoid 80B is operated so that there is a fluid path between the tubings 83B and 85B. This state of the solenoids is controlled by the switch 11. With the solenoids in this position, there is a direct path from the air intake 16 by way of solenoid 80A, via pump 12, and by way of solenoid 80B to chamber 10. This causes a pressurizing in the chamber 10. In this mode of operation the tubings 84A and 84B are essentially disconnected.

For vacuum operation the solenoids 80A and 80B are switched to their alternate position, under control of the switch 11. The switch 11 may be operated manually or may be an electronic switch controlled from the overall processing system. In the vacuum state of operation, the tubings 83A and 83B are blocked and the input side of the pump couples to the chamber 10 by way of solenoid 80B and tubings 84B and 85B. Similarly, the output side of the pump couples to the air source 16 by way of solenoid 80A and the tubings 84A and 85A.

To deliver blood product from the flexible blood product bag, or bags, to the centrifuge for some centrifugation process, the user opens the door to the chamber, hangs the bag(s) on the bag hanger, routes the tubing from the bags to the special tubing fixture that is part of the chamber door, closes the door, attaches the tubing ends to the centrifuge processing bag(s) tubing with sterilized docks, and then starts the computer system which controls the pump and centrifuge process. The computer system is responsible for maintaining the correct pressure level in the chamber derived either from the user, or by some established software protocol. Once the blood products have been completely delivered to the centrifuge, the pump is stopped and the release valve is activated to allow the pressure to escape.

To deliver blood product from centrifuge processing bag or bags, to a flexible blood product bag or bags, the user opens the door to the chamber, hangs the bag(s) on the bag hanger, routes the tubing from the bags to the special tubing fixture that is part of the chamber door, closes the door, attaches the tubing ends to the centrifuge processing bag(s) tubing with sterilized docks, and then starts the computer system which controls the pump and centrifuge process, if it is not already active or running. The computer system is responsible for maintaining the correct vacuum level in the chamber derived either from the user, or by some established software protocol. Once the blood product has been delivered to the flexible blood product bag(s) in the chamber, the pump is stopped and the release valve is activated to allow the vacuum to escape.

Now, reference may be made to separate embodiments of the present invention, such as illustrated in FIGS. 4-7. In one embodiment there may be provided a single pressure/vacuum chamber and a single pump device. Another embodiment may include two pressure/vacuum chamber devices. In still another embodiment there may also be provided separate pumps.

Now, with reference to FIG. 4, there is shown a single pump 12 and a single chamber 10. FIG. 4 also shows the processor control 50 with the control line 52 coupling to the pump 12.

Associated with the processor control 50, may be a solenoid arrangement such as that depicted in FIG. 3 with a switch that is either manually controlled or a computer control switch for selecting either pressure or vacuum operation. FIG. 4 illustrates a series of blood product bags 20 hung within the chamber 10. Also illustrated is the door 28 and the airtight fixture 26. For the pressure application, the chamber is essentially used to empty the contents of the sterile blood bags using pressure that is distributed evenly about the entire outer surfaces of each bag. It is noted in FIG. 4 that the bags are preferably hung vertically but also may be hung in other positions so that there are no air bubbles that would tend to get into the outlet tubing from each of the bags. The applied pressure provides an efficient and accurate way of dispensing blood product from the bags.

Figure 5:
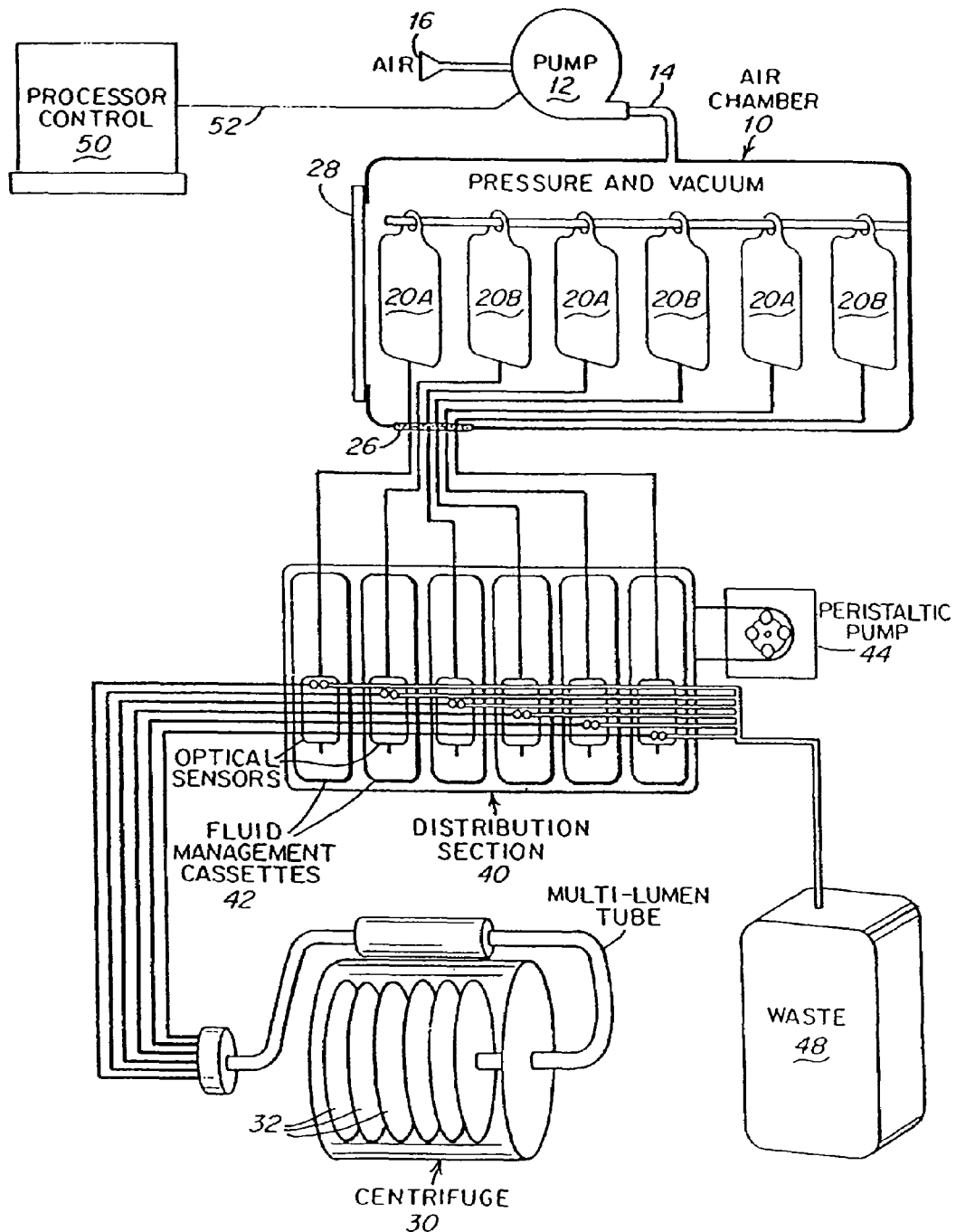
FIG. 5 is a system block diagram of another embodiment of the present invention employing a single pump but in which the chamber can contain blood storage bags that can be alternately emptied and filled.

Reference is now made to another embodiment of the invention illustrated in FIG. 5. In this embodiment it is noted that there are provided two separate series of bags. This includes three bags 20A and three bags 20B. The bags 20A are emptied with the application of pressure and the bags 20B may be filed with the use of vacuum. Again, there is illustrated in FIG. 5 the processor control 50 and control line 52 to the pump 12 for controlling the pump to apply either pressure or vacuum to the chamber 10.

In the sequence of operation in accordance with the embodiment of FIG. 5, blood product in bags 20A may be transferred with the use of pressure to the centrifuge. Thereafter, with the application of vacuum to the chamber 10 some predetermined blood products from the processing bags may be transferred to the bags 20B.

Figure 6:
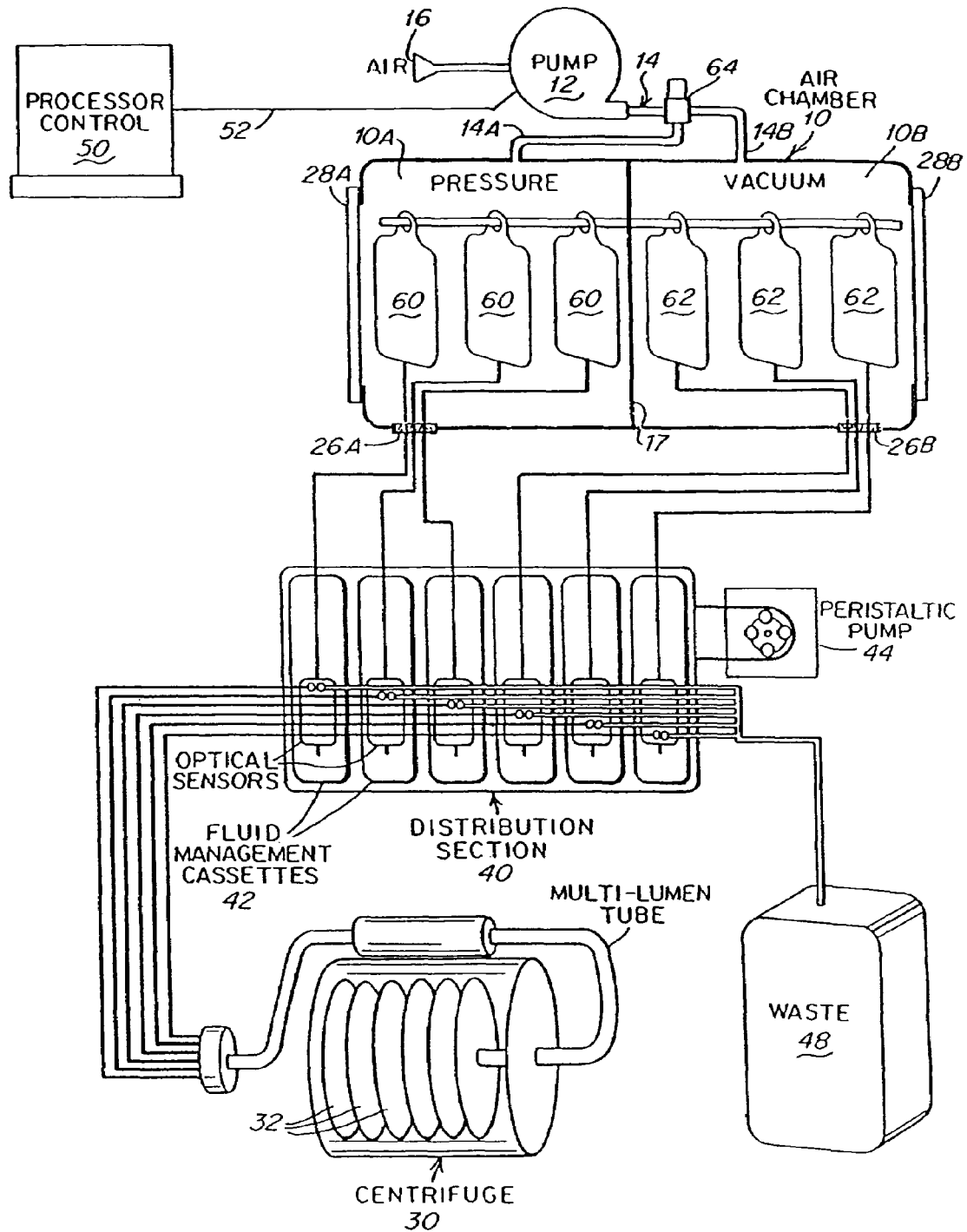
FIG. 6 is a system block diagram of still another embodiment of the present invention in which the airtight containment chamber is separated into two separate chambers with a single pump.

Reference is now made to FIG. 6 for still a further embodiment of the present invention. This embodiment includes airtight containment chambers 10A and 10B within one single chamber 10. These chambers 10A and 101B are separated by a barrier or dividing wall 17. It is noted that, within each chamber, there are hangers. Within chamber 20A a series of bags 60 are hung from one hanger. On the other side, in chamber 10B there are a series of bags 62 that are hung from a hanger within that chamber. There are also illustrated in FIG. 6 separate doors 28A and 28B and respective airtight fixtures 26A and 26B.

In FIG. 6 there is illustrated a single pump 12 that may have associated therewith a solenoid 64 for separating the output of the pump into two lines or tubings 14A and 14B. This arrangement may provide pressure in one chamber, such as chamber 10A and vacuum in the second chamber, such as chamber 10B.

In accordance with one version of the embodiment of FIG. 6, there solenoid 64 may be operated to provide, during a first sequence of operation, pressure into chamber 10A, and during a second sequence of operation, vacuum into chamber 10B. Alternatively, the connections at the solenoid 64 may be provided so that both the input and output ends of the pump connect to tubings 14A and 14B so that pressure and vacuum occur sequentially in the respective chambers 10A and 10B. In this way, one chamber contains bags that are to be emptied using pressure, and a second chamber contains bags that are to be filled using a vacuum.

Figure 7:
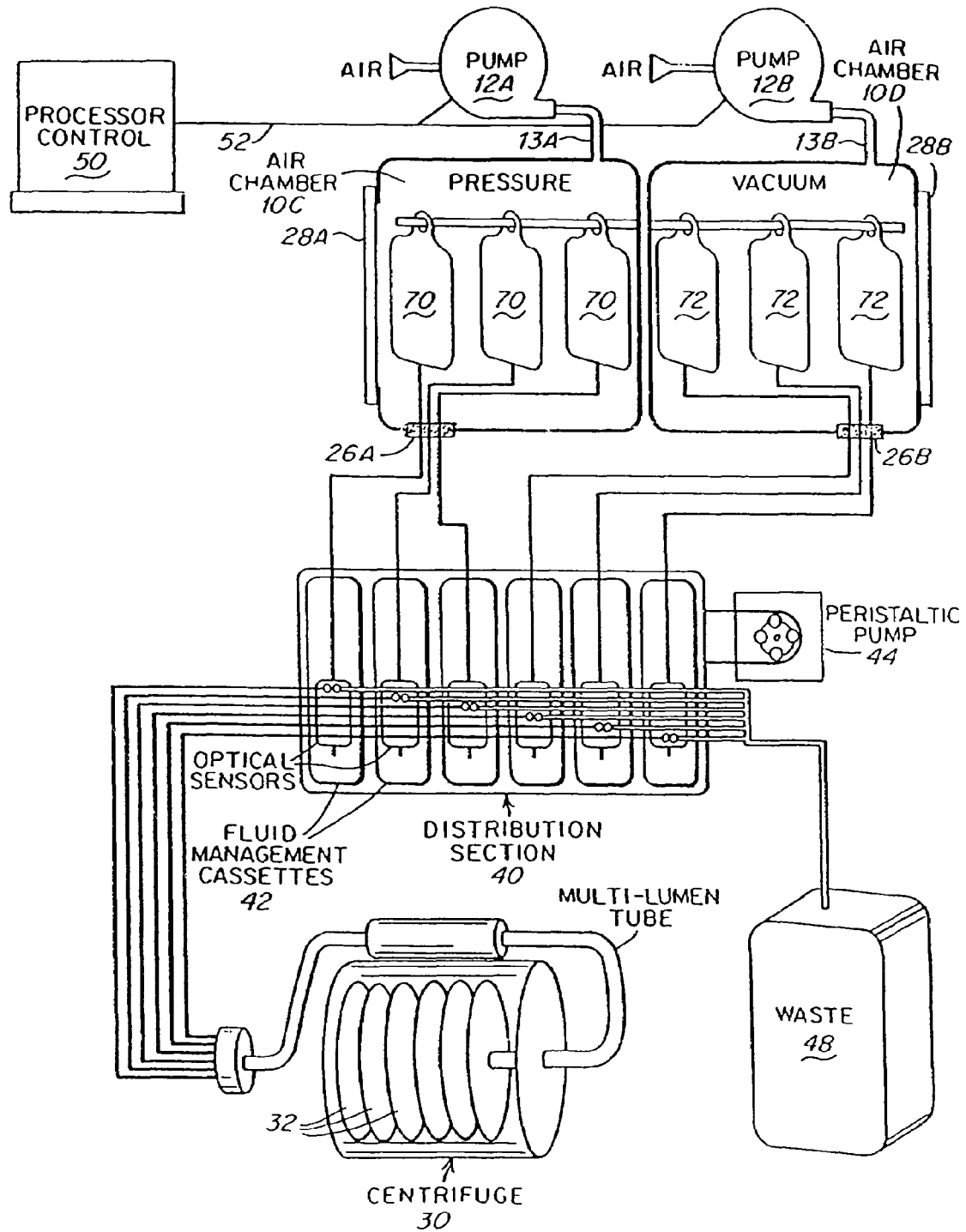
FIG. 7 is a system block diagram for still another embodiment of the present invention employing separate containment chambers and separate pumps.

Now, reference is also made to still a further embodiment of the present invention illustrated in FIG. 7. This embodiment now uses two separate chambers 10C and 110D. Each of these have respective doors 28A and 28B and airtight fixtures 26A and 26B. The chamber 10C is for housing bags 70 and is considered as the pressure chamber. The chamber 10D houses bags 72 and is considered as the vacuum chamber. In FIG. 7 the pump 12A is operated so as to provide pressure by way of tubing 13A to the chamber 10C. Alternatively, the pump 12B is operated to draw vacuum through the tubing 13B so that the chamber 10D is under vacuum. It is also noted in FIG. 7 that the processor control 50 includes a control line 52 that is considered coupling to both of the pumps 12A and 12B. The control is more simplified in the version of FIG. 7 in that there is a pump associated with each chamber. The previous embodiments described in FIGS. 4-7, require a switching mechanism so that switching can occur between vacuum and pressure within the chamber. No such switch between the pump and chamber is required in the version of FIG. 7.

Having now described a few embodiments of the invention, it should be apparent to those skilled in the art that the foregoing is merely illustrative and not limiting, having been presented by way of example only. Numerous modifications and other embodiments are within the scope of ordinary skill in the art and are contemplated as falling within the scope of the invention as defined by the appended claims and equivalents thereto. The contents of all references, issued patents, and published patent applications cited throughout this application are hereby incorporated by reference. The appropriate components, processes, and methods of those patents, applications and other documents may be selected for the present invention and embodiments thereof.

What is claimed is:

1. A centrifuge processing system for handling blood products, said system comprising:
   a centrifuge including therein at least one centrifuge processing bag;
   a storage module including an airtight containment chamber for supporting a plurality of blood product storage bags in an upright position with a tubing end of each of the blood product storage bags at the bottom thereof, an access door to the chamber, and a fluid pump coupled to the airtight containment chamber for establishing one of pressure and vacuum within the chamber to transfer blood product in either direction between at least one of the plurality of blood product storage bags and the at least one centrifuge processing bag;
   a single airtight fixture including in a wall of the airtight chamber configured such that respective tubing extending from the tubing end of each of the plurality of blood product storage bags exits the chamber through the single airtight fixture; and
   a control module for controlling operation of the fluid pump to effect the transfer of blood product between at least one of the plurality of blood product storage bags and the at least one centrifuge.

2. A system as in claim 1 wherein said at least one centrifuge processing bag is a sterile centrifuge processing bag.

3. A system as in claim 2 wherein the blood storage product bags are disposed in a position that allows for blood product flow due to pressure or vacuum without allowing a blockage to occur via a collapsed tube or blood storage bag.

4. A system as in claim 1 wherein said fluid pump comprises an air pump having a compressor for delivering either a pressure to the chamber or drawing a vacuum on the chamber.

5. A system as in claim 4 including a control solenoid circuit for selecting, in one state, pressure operation and in another state, vacuum operation.

6. A system as in claim 1 further including a fluid control circuit that couples, only one at a time, either pressure of vacuum to the chamber.

7. A system as in claim 6 wherein some of the bags in the chamber are subjected to pressure during a first time interval and other of the bags are subjected to vacuum during a second time interval.

8. A system as in claim 1 including a pair of airtight containment chambers one for receiving a vacuum source and the other for receiving a pressure source.

9. A system as in claim 8 including an air control circuit coupled between the pump and the chambers for directing only pressure to one chamber and only vacuum to the other chamber.

10. A system as in claim 8 including a pair of pumps, one for each chamber.

11. A system as in claim 10 wherein only vacuum is coupled to one chamber and only pressure is coupled to the other chamber.

12. A system as in claim 11 wherein the chambers are separated and each has its own access door.

* * * * *